United States Patent
Mack et al.

[11] Patent Number: 6,149,872
[45] Date of Patent: Nov. 21, 2000

[54] MODULAR REAGENT CARTRIDGE

[75] Inventors: Michael Mack, Hanau; Peter Nebel, Erlenbach; Peter Stoerk, Seligenstadt, all of Germany

[73] Assignee: Byk-Sangtec Diagnostica GmbH & Co. KG, Dietzenbach, Germany

[21] Appl. No.: 09/068,088

[22] PCT Filed: Oct. 30, 1996

[86] PCT No.: PCT/EP96/04705

§ 371 Date: Jun. 29, 1998

§ 102(e) Date: Jun. 29, 1998

[87] PCT Pub. No.: WO97/16734

PCT Pub. Date: May 9, 1997

[30] Foreign Application Priority Data

Nov. 2, 1995 [DE] Germany .......................... 195 40 877

[51] Int. Cl.$^7$ .............. G01N 35/10; B01L 9/00; B65D 21/02
[52] U.S. Cl. .......................... 422/102; 422/63; 422/104; 206/504; 206/509; 220/23.4; 220/23.8
[58] Field of Search ............... 422/63, 65, 102, 422/103, 104; 436/43, 47; 206/504, 509; 220/23.4, 23.8; 215/10

[56] References Cited

U.S. PATENT DOCUMENTS

| 3,521,785 | 7/1970 | Bergmann et al. ............... 220/23.4 |
| 3,617,222 | 11/1971 | Matte ........................ 23/230 |
| 3,713,985 | 1/1973 | Astle ......................... 422/102 |
| 4,685,565 | 8/1987 | Sparling .................... 206/427 |
| 4,849,177 | 7/1989 | Jordan ....................... 422/64 |
| 4,944,924 | 7/1990 | Mawhirt et al. .............. 422/104 |
| 4,956,148 | 9/1990 | Grandone .................... 422/64 |
| 5,104,807 | 4/1992 | Mitsumaki et al. ............. 436/47 |
| 5,186,339 | 2/1993 | Heissler ..................... 211/74 |
| 5,201,232 | 4/1993 | Uffenheimer ................. 73/864.23 |
| 5,322,668 | 6/1994 | Tomasso ..................... 422/104 |
| 5,350,564 | 9/1994 | Mazza et al. ................. 422/63 |
| 5,397,542 | 3/1995 | Nelms et al. ................ 422/104 |
| 5,616,301 | 4/1997 | Moser et al. ................ 422/104 |

FOREIGN PATENT DOCUMENTS

| 2132813 | 4/1995 | Canada ............. G01N 35/00 |
| 435 481 | 7/1991 | European Pat. Off. ...... G01N 35/00 |
| 642 831 | 8/1994 | European Pat. Off. ...... B01L 7/00 |
| 0 651 254 | 10/1994 | European Pat. Off. ...... G01N 35/00 |
| 920 518 | 7/1949 | Germany . |
| 2 134 808 | 1/1972 | Germany ............. B01L 11/00 |
| 2 152 068 | 4/1972 | Germany ............. C12K 1/00 |
| 1 575 122 | 6/1974 | Germany ............. B01L 9/06 |
| 40 23 194 | 1/1992 | Germany ............. G01N 35/02 |
| WO 94/13402 | 6/1994 | WIPO ............... B01L 3/00 |

Primary Examiner—Long V. Le
Attorney, Agent, or Firm—Jacobson, Price, Holman & Stern, PLLC

[57] ABSTRACT

The invention concerns a modular reagent cartridge (10) which includes a plurality of reagent containers (12 to 18) directly interconnected by integrally formed coupling devices (22). The connection is brought about by form-locking rail guides.

11 Claims, 2 Drawing Sheets

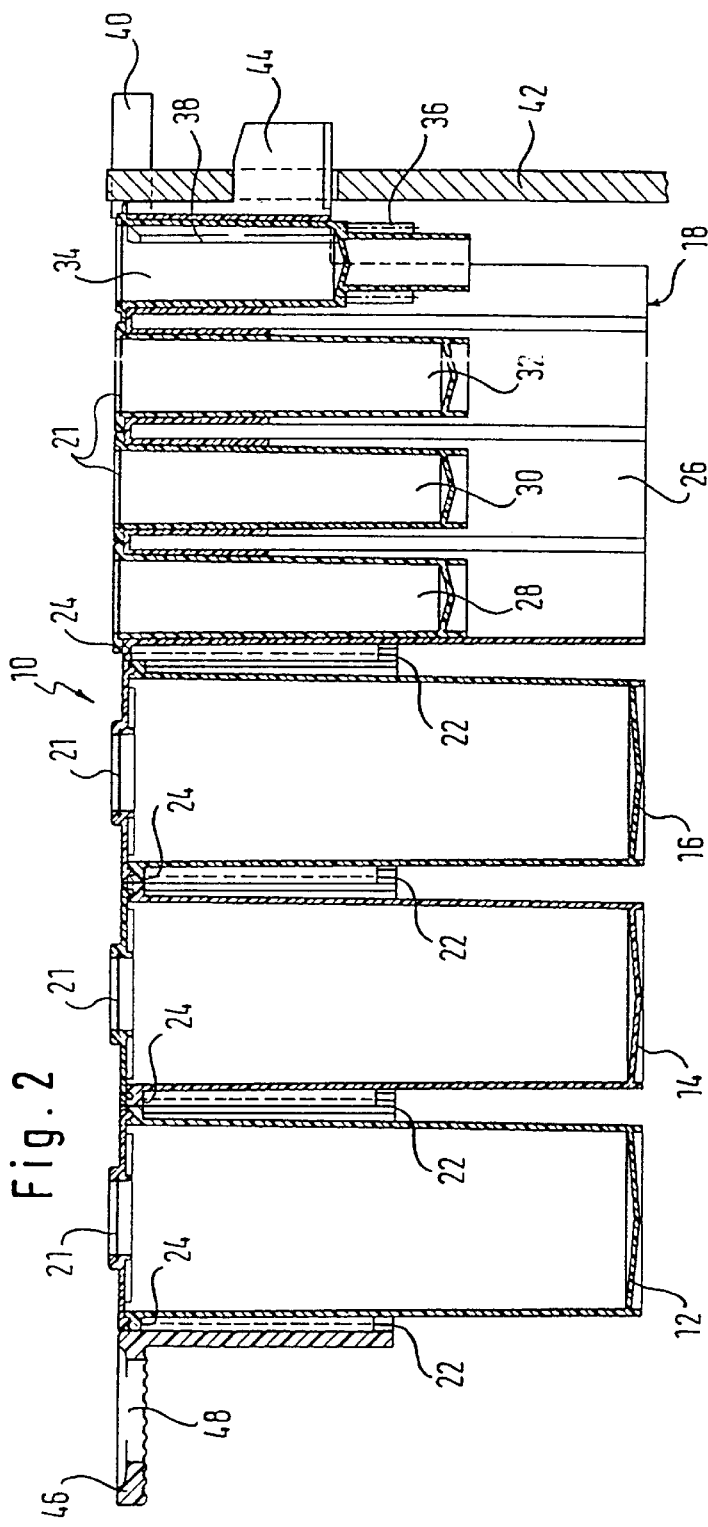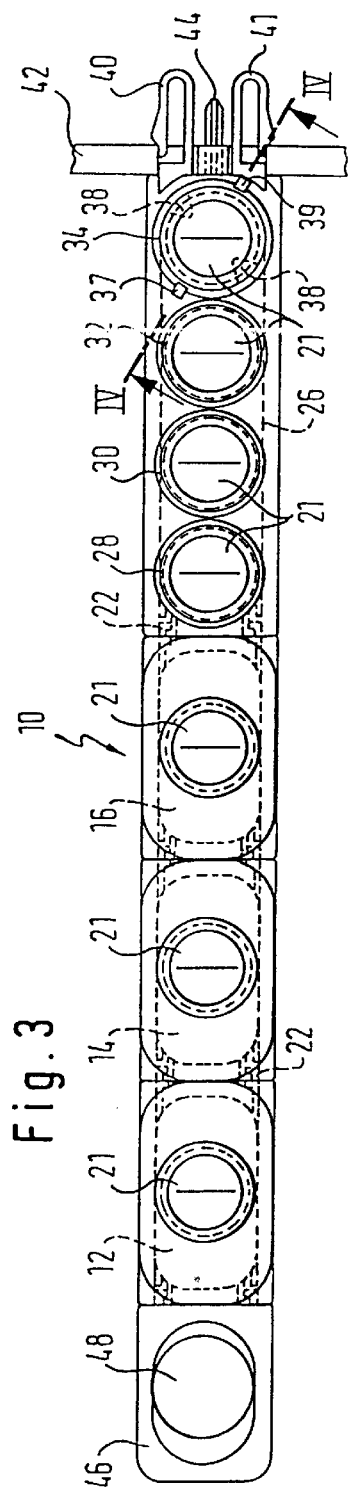

MODULAR REAGENT CARTRIDGE

The present invention relates to a reagent cartridge for the supply of ready-to-use, biochemical reagents in liquid form, whose purpose is to enable a simple loading into and use in a fully automatic analyzer.

Reagent vessels are known in principle from the prior art. Thus, for example, the EP 0 564 970 A3 describes a socalled reagent kit, which contains three reagent vessels in a square frame. The floor and the lid of the housing have openings, which allow air to circulate through the interior of the housing, in order to guarantee uniform cooling of the reagent vessels.

The EP 0 435 481 A2 describes an analyzer with a rotating disk, on which the reagent vessels are arranged. Every two of the vessels, which have the shape of a piece of cake, are connected together into a double package by means of a lid that can be snapped on. To facilitate production, the double package can also be designed as one piece.

Finally the EP 0 502 638 A2 describes an automatic analyzer with a plurality of longitudinal reagent vessels, which are transported by an automatic handling system. To enable the transport of these reagent vessels, they are provided wish lateral flanges and projections.

The invention is based on the problem of providing a means for handling reagents, which enables flexible handling even with the most varying reagent charges.

This problem is solved by the features of claim 1. According to the invention, a modular reagent cartridge is provided that is produced by connecting several reagent vessels directly Lo each other by means of coupling devices moulded on as one piece.

The invention provides, first of all, a modular system of reagent vessels, whereby the individual vessels can be connected into a reagent cartridge by means of coupling devices that are moulded on in one piece. Such a cartridge can then be inserted into an analyzer with only one manipulation. Furthermore, owing to the modular construction of the reagent cartridge the reagent vessels can be processed individually during the filling process; and, following completed production, these reagent vessels can be assembled into a reagent cartridge in a single fabrication step. In so doing, no other coupling elements or the like are necessary. Rather the individual reagent vessels are connected directly to each other without intercalation of additional connecting elements. Thus, arbitrary combinations of the most varying reagent charges are always guaranteed. Thus, the reagent cartridge of the invention offers handling advantages that did not exist before and that also save time especially in the course of the production process, since the reagent vessels can be filled in the onassembled state; and following fabrication of the cartridges they can be handled as one unit. At the same time any defective vessels can be replaced easily with new vessels, without having to replace the entire cartridge. In addition, it is possible to combine together in one cartridge reagent vessels of varying sizes and/or volume, whereby the combination may be arbitrary. This means simultaneously that a large number of different reagent cartridges does not have to be prepared. Rather each cartridge can be put together individually with the desired combination of vessels.

Advantageous embodiments of the invention are disclosed in the dependent claims.

According to a first advantageous embodiment, at least one reagent vessel may exhibit a preferably snap-in connecting device, in order to produce a force-locking connection between the reagent cartridge and an analyzer. Such a reagent vessel, which can constitute to some extent a base element of the modular system, enables a force-locking connection between the reagent cartridge and the analyzer, which can be produced arbitrarily often and readily disconnected again owing to the special locking mechanism. The locking connection is also moulded on advantageously as one piece to the reagent vessel.

According to another design of the invention, a reagent vessel comprises a holding frame and at Least one container, which has less volume than a reagent vessel. This embodiment also enables the use of small volume reagent containers, which are received in the holding frame, which in turn forms a module of the system. The advantage is simultaneously that several of the containers with less volume can also be received in a single holding frame, whereby one and the same holding frame is also suitable for several containers with different volumes.

It is especially advantageous when at least one container is received so as to rotate in the holding frame and, in so doing, exhibits preferably a moulded-on toothed rim. Owing to the rotatable accommodation, the container can carry out a rotational motion around its vertical axis preferably by means of the moulded-on toothed rim, in order to mix a suspension contained in the container. In this respect it is especially advantageous, when the holding frame is designed partially open, in such a manner that there is access to one side or bottom side of the container. Thus a drive can be coupled to the container, so that it is out in rotation. Such a drive can occur, for example, by means of a toothed wheel or a toothed rack. Several of the containers can also be provided with toothed rims or the like, so that the drive has to engage with only one of the containers. Owing to the transfer of the motion of rotation, several of the containers, received in the holding frame, can then be put in rotation.

According to another design of the invention, the container, received in the holding frame, is attached. In so doing, it is guaranteed that the container does not fall inadvertently out of the holding frame and that upon being put in rotational motion the container always remains tn the same place in the frame. At the same time the attachment can be done advantageously by means of latches, which limit travel elasticly, a feature that guarantees very fast and simple manipulation.

Furthermore, it is advantageous when the reagent cartridge of the invention exhibits a handle with a coupling device that is moulded on in one piece. Such a handle can be coupled in the same manner as the reagent vessels to the reagent cartridge, so that good manipulation of the reagent cartridge is ensured, especially when a plurality of the reagent cartridges are arranged side-by-si(ie. In this case it is especially advantageous, when the handle exhibits a finger opening, since then the cartridge can be pulled out of the analyzer with only one finger. To increase the flexibility of the modular reagent cartridge, the handle can also exhibit an extension element, which is preferably moulded on as one piece and which is equivalent to the length of at least one reagent vessel. Thus, a constant length of the reagent cartridge is guaranteed, even when a vessel is less coupled, since the handle compensates for the length of the missing vessel.

The coupling device, envisaged according to the invention, can be made in an advantageous manner by means of shape-locking rail guides, which automaticly look in the coupled state. In so doing, the individual reagent vessels need only to be "telescoped" it the rail guides, a feature that enables very fast manipulation. The cross section of the rail guides may exhibit any suitable shape; for example, they may be rectangular or dovetailed. However, it is especially advantageous when the rail guide exhibits a stop. Thus, during the fabrication of the reagent cartridge one does not have to pay attention that all of the reagent vessels lie flush with the upper side, since this is guaranteed by the envisaged stop.

According to another advantageous design of the invention, the reagent vessels exhibit the same length arid/or width, i.e. the container dimensions are the same in one dimension. The result is a cartridge having uniform shape, i.e. constant width.

To protect the vessels, the reagent cartridge may exhibit a lid that can be put or and which is put on the upper side of the cartridge.

Finally it is especially advantageous when the outside of the reagent cartridge forms at least in part a largely flat, continuous surface, which extends over the reagent vessels. In so doing, a label, which shows all of the relevant, test-specific data in coded form, can be affixed smoothly on the outside of the reagent cartridge, even though it comprises several reagent vessels.

In the following one advantageous embodiment of the invention is described purely as an example with reference to the attached drawings.

FIG. 2 is a cross section of the reagent cartridge of FIG. 1.

FIG. 3 is a top view of the reagent cartridge of FIG. 1; and

Figure 1:
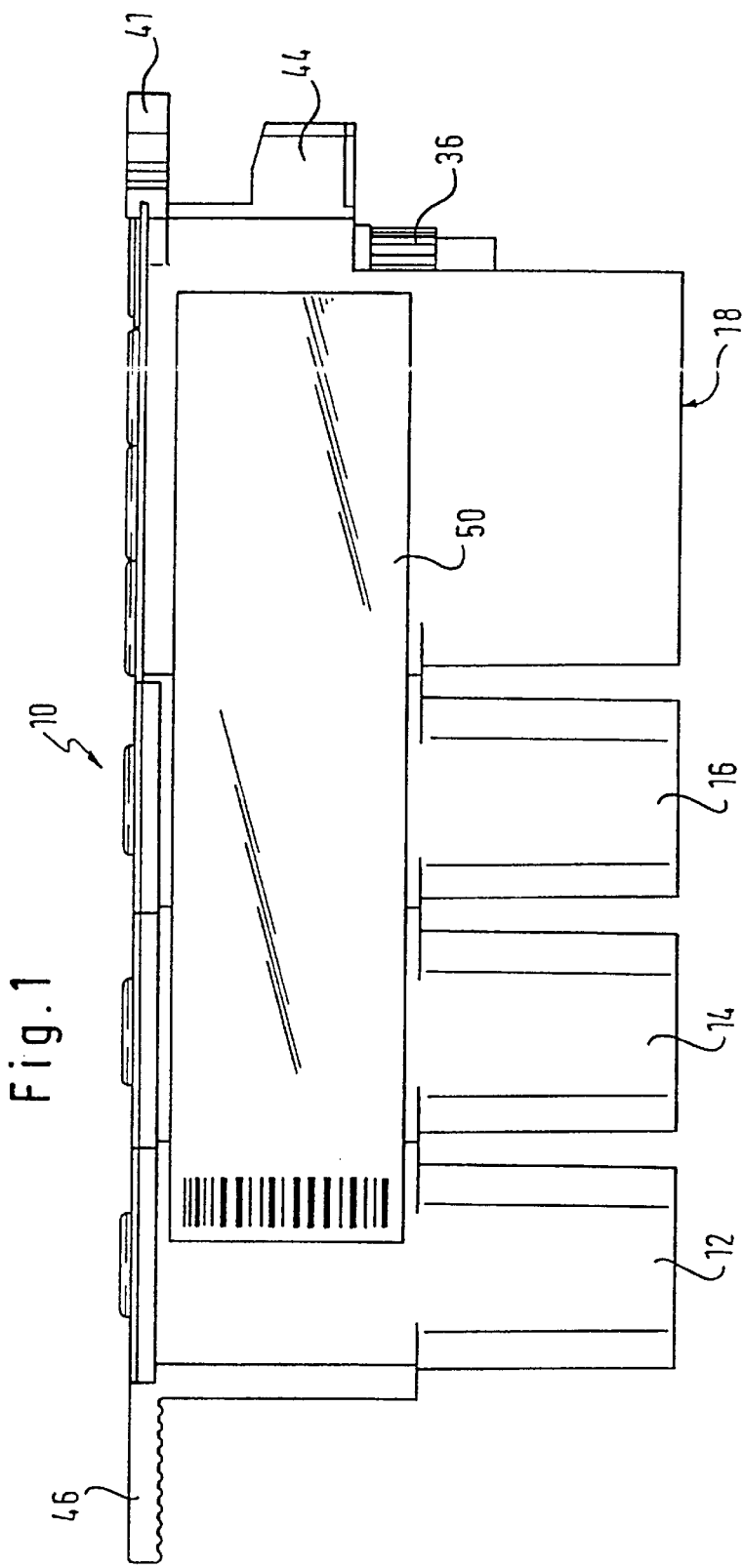
FIG. 1 is a side view of a modular reagent cartridge.

The modular reagent cartridge 10, which is depicted in FIG. 1, is constructed by connecting directly to each other several reagent vessels 12, 14, 16 and 18 by means of coupling devices, moulded-on as one piece. In so doing, the reagent vessels 12, 14 and 16 are designed the same and comprise an essentially square-shaped vessel, which is sealed with a rubber disk 21, which is made of silicone, is slit, enables the filling of the reagent vessels in one special manufacturing step, and enables automatic removal of the aliquots in reagent positions in the analyzer. The type and shape of the slit, which can be designed in the shape of a cross, star or straight line, is preferably constructed in such a manner that it seals again following extraction of the filling mandrel of a filling machine or pipetting needle of the analyzer.

As FIG. 2 shows, the coupling device, which is moulded on as one piece to the reagent vessels, comprises shape-locking rail guides 22, which exhibit a rectangular cross section and are telescoped, whereby the individual reagent vessels form the depicted reagent cartridge. At the upper end of the rail guide 22, the upper rim of the reagent vessels 12 to 18 is slid into the region of the rail guides 22, so that a stop 24 is formed that ensures an aligned telescoping of the the reagent vessels. The rail guides 22 are formed in such a manner that one side of a reagent vessel exhibits a pair of U-shaped rails, as seen from the cross section, whereby the openings of the "U" face each other. These rails that are spaced in parallel form to some extent a rectangular cross section, into which the rails of the reagent vessels to be coupled can be slid. These rails are located on the other side of a reagent vessel and are L shaped in the cross section, whereby in coupling two vessels together one leg of the "L" slides in one of the rails, exhibiting a U-shaped cross section. To obtain an automatic locking of the reagent vessels upon reaching the stop 24, one leg of the rails, exhibiting a U-shaped cross section, is designed slightly wedge-shaped, so that upon sliding in the reagent vessels to be coupled, there is a slight locking effect, which reaches its maximum as soon as the stop 24 is reached. Finally the ends of the rails, whose cross section exhibits an L-shape, exhibit an extension, which is provided with feed slopes to facilitate the "threading".

The reagent vessel 18, depicted in the Figures, is formed by a holding frame 26, which receives in total four containers 28, 30, 32, and 34, which exhibit less volume than the reagent vessels 12, 14 and 16. The containers 28 to 34 have an essentially cylindrical shape and are also sealed with a protected rubber disk 21 on the upper side. In so doing, the containers 28 to 34 are put into appropriate chambers in the holding frame 26.

All of the containers 28 to 34 are received rotatably in the holding frame 26, whereby the bottom side of the container 34 exhibits a moulded-on toothed rim 36. The holding frame 26) is designed open in its rear region, i.e. in the region of the toothed rim 36, so that access to the toothed rim 36 is possible from the direction of the right side, as shown in FIGS. 1 to 3. Thus, to mix a suspension contained in the container 34, a drive can occur over a toothed rack or a toothed wheel. Owing to this drive, the container 34 is put in 180□ rotation around its longitudinal axis. To obtain suspensions as homogeneous suspensions, interior ribs 38 (cf. FIG. 3), which extend in the longitudinal direction and which are oriented axially parallel, are moulded to the interior wall of the container 34. Thus during the rotational motion around the vertical axis the mixed product is pushed away from the ring area near the shell of the container while forming a vortex in the direction of the axially central removal area.

Figure 4:
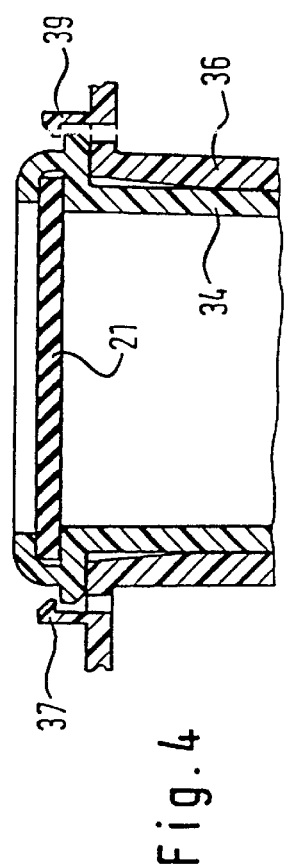
FIG. 4 is a cross section along the line IV—IV in FIG. 3.

As FIG. 4 shows, the container 34 is attached in the holding frame 36 by two latches 37, 39, which reach over one edge of the container. Owing to the flexible design of the latches, the container 34 can be pushed into or removed from the position shown in FIG. 4. In place of the container 34, however, a container 28 to 32 can also be inserted into the chamber, shown on the far right in FIG. 2.

A connecting device is moulded to the right side of the holding frame 26, as shown in FIGS. 1 to 3, i.e. to the rear end of the reagent cartridge, in the shape of two flexible locking bows 40, 41, which produce a force-locking connection between the reagent cartridge 10 and an analyzer. In FIG. 2 an assembly wall 42 of an analyzer is indicated schematicly; said wall exhibits suitable openings, into which the locking bows 40 and 41 can snap. Owing to the flexible design of the essentially Li-shaped locking bows and owing to the latches, provided on the free end of the locking bows, the reagent cartridge can be inserted arbitrarily often and easily into the corresponding openings of the assembly wall 42 and is thus connected force-lockingly to the analyzer. A vane 44, which is provided below the locking bows and which is also moulded on as one piece, serves to activate a sensor device, for example a light barrier, in order to inform the analyzer that the reagent cartridge is properly installed in the analyzer.

A handle 46, which also exhibits a rail guide, which is moulded on in one piece, and with which it is coupled to the reagent vessel 12, is located on the left side of the reagent cartridge, i.e. on the front side, as shown in FIGS. 1 to 3. The handle is L-shaped and exhibits on its shorter leg a finger opening 48, into which a finger can reach.

To the extent a reagent cartridge is put together in which, for example, there are only two of the vessels 12 to 16, a handle can be used whose horizontal leg exhibits a moulded-on extension element, which is equivalent to the length of the missing reagent vessel. Thus the length of the reagent cartridge can be held constant.

As FIG. 1 shows, the sides of all of the reagent vessels 12 to 18 are designed in such a manner over approximately half the height of the container that a flat, continuous surface, extending over the reagent vessels 12 to 18, is formed on the outside of the reagent cartridge. To this end, the vessels, whose cross sections exhibit rounded off edges, are designed in such a manner in their upper region, .e. in the region of the rail guides 22, that the continuous surface is formed after the reagent vessels are coupled together. A label 50, containing the necessary data, can then be glued smoothly on this surface.

The upper edge of all of the reagent vessels is constructed in such a manner that one edge has sufficient area to attach a liquid-tight seal, e.g. a heat sealing film. Furthermore, it is guaranteed that the heat sealing film can be removed again without any problems, a feature that is attained in that a master seal is connected by means of an adhesive connection to the hot sealing film, which is also removed then upon removal of the master seal. In so doing, the master seal is affixed over the entire reagent cartridge in one working step and in so doing also covers the locking bows 40, 41 of the coupling device. Thus, it is ensured that before insertion into the analyzer the master seal has to be removed by the user by simply pulling it off from the reagent cartridge.

On the grounds of the above description it should be clear that the invention is not limited to the vessel sizes and types that are presented here and that can be used in varying numbers in the reagent cartridge. All of the reagent vessels and also the handle are made preferably of immunologic inert plastic, such as polypropylene. However, the volume of the vessels may vary depending on the need.

What is claimed is:

1. A modular reagent cartridge comprising adjacent reagent vessels, at least one of which is for directly receiving a reagent; each of the reagent vessels being connected directly to another of the reagent vessels by means of a one-piece moulded coupling device having a shape-locking, wedge-shaped rail guide which automatically locks in coupled state and which has a stop which provides an aligned telescoping of the reagent vessels and locking at the stop.

2. A reagent cartridge, as claimed in claim 1, wherein at least one of the reagent vessels has a snap-in connecting device, which is capable of producing a force-locking connection between the reagent cartridge and an analyzer.

3. A reagent cartridge, as claimed in claim 1, further comprises a holding frame and at least one container which has a smaller volume than a reagent vessel.

4. A reagent cartridge, as claimed in claim 3, wherein the container is attached to the holding frame.

5. A reagent cartridge as claimed in claim 4, wherein the container is attached to the holding frame by latches.

6. A reagent cartridge, as claimed in claim 1, wherein the coupling device has a moulded on handle.

7. A reagent cartridge, as claimed in claim 1, wherein the handle has an extension element, which is equivalent in length to the length of at least one of the reagent vessels.

8. A reagent cartridge, as claimed in claim 6, wherein the handle has a finger opening.

9. A reagent cartridge, as claimed in claim 1, wherein the outside of the reagent cartridge forms an essentially flat, continuous surface, which extends over the reagent vessels.

10. A modular reagent cartridge comprising adjacent reagent vessels, a holding frame and at least one container, each of the reagent vessels being directly connected to another by a one-piece molded-on coupling device;

a reagent vessel of which comprises the holding frame and at least one container which has a volume which is less than that of the reagent vessel, is rotatably mounted in said holding frame and has a molded-on toothed rim.

11. A reagent cartridge, as claimed in claim 10, wherein the holding frame is partially open, to provide access to one side or bottom of the container.

* * * * *